(12) United States Patent
Konesky

(10) Patent No.: US 11,129,665 B2
(45) Date of Patent: Sep. 28, 2021

(54) MIXING COLD PLASMA BEAM JETS WITH ATMOPSHERE

(71) Applicant: Bovie Medical Corporation, Clearwater, FL (US)

(72) Inventor: Gregory A. Konesky, Hampton Bays, NY (US)

(73) Assignee: Apyx Medical Corporation, Clearwater, FL (US)

( * ) Notice: Subject to any disclaimer, the term of this patent is extended or adjusted under 35 U.S.C. 154(b) by 522 days.

(21) Appl. No.: 15/778,474

(22) PCT Filed: Dec. 2, 2016

(86) PCT No.: PCT/US2016/064537
§ 371 (c)(1),
(2) Date: May 23, 2018

(87) PCT Pub. No.: WO2017/096112
PCT Pub. Date: Jun. 8, 2017

(65) Prior Publication Data
US 2019/0254734 A1 Aug. 22, 2019

Related U.S. Application Data

(60) Provisional application No. 62/261,914, filed on Dec. 2, 2015.

(51) Int. Cl.
*A61B 18/04* (2006.01)
*B23K 10/00* (2006.01)
(Continued)

(52) U.S. Cl.
CPC ........ *A61B 18/042* (2013.01); *A61B 17/3209* (2013.01); *A61B 18/1402* (2013.01);
(Continued)

(58) Field of Classification Search
CPC .............. A61B 18/042; A61B 18/1402; A61B 2018/00583; A61B 2018/00601;
(Continued)

(56) References Cited

U.S. PATENT DOCUMENTS 1,889,609 A   11/1932   Arthur
2,835,254 A   5/1958    Coles
(Continued)

FOREIGN PATENT DOCUMENTS

CN   101134203 A   3/2008
CN   103537245 A   1/2014
(Continued)

OTHER PUBLICATIONS

International Search Report and Written Opinion for PCT Application No. PCT/US2016/064537; dated Feb. 21, 2017; ten (10) pages.
(Continued)

*Primary Examiner* — Tigist S Demie
(74) *Attorney, Agent, or Firm* — Gerald Hespos; Michael Porco; Matthew T. Hespos

(57) ABSTRACT

The present disclosure is directed to an electrosurgical apparatus for generating plasma in electrosurgical applications. The electrosurgical apparatus includes an end effector disposed on a distal portion of a tube of the electrosurgical apparatus. The end effector mixes ambient air with an inert gas to increase the production of radical species. In one aspect of the present disclosure, the end effector includes a cylindrical augmenter disposed over a distal end of the tube with one or more tilted vanes disposed between the cylindrical augmenter and the tube. In another aspect of the present disclosure, the end effector includes one or more tilted vanes disposed on an inner surface of a wall of the distal end of the tube. In another aspect of the present disclosure, the end effector includes one or more advection apertures on the wall of the distal end of the tube.

18 Claims, 9 Drawing Sheets

Use of an Augmenter to improve mixing.

(51) Int. Cl.
*A61L 2/14* (2006.01)
*A61B 18/14* (2006.01)
*A61B 17/3209* (2006.01)
*A61L 2/02* (2006.01)
*A61B 18/00* (2006.01)
*A61B 18/12* (2006.01)

(52) U.S. Cl.
CPC .............. *A61L 2/02* (2013.01); *A61L 2/14* (2013.01); *B23K 10/00* (2013.01); *A61B 2018/00583* (2013.01); *A61B 2018/00601* (2013.01); *A61B 2018/00744* (2013.01); *A61B 2018/1213* (2013.01); *A61B 2018/1412* (2013.01)

(58) Field of Classification Search
CPC .. A61B 2018/00744; A61B 2018/1213; A61B 17/32035; A61B 2018/00017; A61L 2/02; A61L 2/14
See application file for complete search history.

(56) References Cited

U.S. PATENT DOCUMENTS

| | | | |
|---|---|---|---|
| 3,299,384 A | 1/1967 | Hua-Tung | |
| 3,577,030 A | 5/1971 | Cusick et al. | |
| 3,601,126 A | 8/1971 | Estes | |
| 3,949,266 A | 4/1976 | Vogts et al. | |
| 3,970,088 A | 7/1976 | Morrison | |
| 3,987,795 A | 10/1976 | Morrison | |
| 4,040,426 A | 8/1977 | Morrison, Jr. | |
| 4,041,952 A | 8/1977 | Morrison, Jr. et al. | |
| 4,043,342 A | 8/1977 | Morrison, Jr. | |
| 4,060,088 A | 11/1977 | Morrison, Jr. et al. | |
| 4,255,735 A | 3/1981 | Liautaud | |
| 4,429,694 A | 2/1984 | McGreevy | |
| 4,492,231 A | 1/1985 | Auth | |
| 4,547,721 A | 10/1985 | Drapp | |
| 4,559,943 A | 12/1985 | Bowers | |
| 4,781,175 A | 11/1988 | McGreevy et al. | |
| 4,818,916 A | 4/1989 | Morrisroe | |
| 4,887,005 A | 12/1989 | Rough et al. | |
| 4,890,610 A | 1/1990 | Kirwan et al. | |
| 4,897,285 A | 1/1990 | Wilhelm | |
| 4,901,719 A | 2/1990 | Trenconsky et al. | |
| 4,901,720 A | 2/1990 | Bertrand | |
| 4,999,597 A | 3/1991 | Gaynor | |
| 5,088,997 A | 2/1992 | Delahuerga et al. | |
| 5,302,881 A | 4/1994 | O'Loughlin | |
| 5,325,019 A | 6/1994 | Miller et al. | |
| 5,669,904 A | 9/1997 | Platt, Jr. et al. | |
| 5,710,486 A | 1/1998 | Ye et al. | |
| 5,717,293 A | 2/1998 | Sellers | |
| 5,776,092 A | 7/1998 | Farin et al. | |
| 5,801,489 A | 9/1998 | Chism, Jr. et al. | |
| 5,815,047 A | 9/1998 | Sorensen et al. | |
| 5,917,286 A | 6/1999 | Scholl et al. | |
| 6,046,546 A | 4/2000 | Porter et al. | |
| 6,099,525 A | 8/2000 | Cosmescu | |
| 6,154,376 A | 11/2000 | Dan-Harry | |
| 6,170,668 B1 | 1/2001 | Babko-Malyi | |
| 6,181,068 B1 | 1/2001 | Hur et al. | |
| 6,213,999 B1 | 4/2001 | Platt, Jr. et al. | |
| 6,222,321 B1 | 4/2001 | Scholl et al. | |
| 6,262,538 B1 | 7/2001 | Keller | |
| 6,492,951 B1 | 12/2002 | Harris et al. | |
| 6,529,389 B2 | 3/2003 | Perlick et al. | |
| 6,627,163 B1 | 9/2003 | Awakowicz et al. | |
| 6,764,658 B2 | 7/2004 | Denes et al. | |
| 6,807,069 B2 | 10/2004 | Nieminen et al. | |
| 6,852,112 B2 | 2/2005 | Platt | |
| 7,070,144 B1 | 7/2006 | DiCocco et al. | |
| 7,275,013 B1 | 9/2007 | Matlis et al. | |
| 7,316,682 B2 | 1/2008 | Konesky | |
| 7,615,933 B2 | 11/2009 | Hooke et al. | |
| 7,630,774 B2 | 12/2009 | Kami et al. | |
| 7,913,351 B2 * | 3/2011 | Moriya ............ H01L 21/67069 15/320 |
| 7,928,338 B2 | 4/2011 | Suslov | |
| 8,057,468 B2 | 11/2011 | Konesky | |
| 8,267,884 B1 | 9/2012 | Hicks | |
| 8,377,388 B2 | 2/2013 | Konesky | |
| 8,383,038 B2 | 2/2013 | Kitano | |
| 8,409,190 B2 | 4/2013 | Konesky et al. | |
| 8,795,265 B2 | 8/2014 | Konesky et al. | |
| 8,802,022 B2 | 8/2014 | Konesky | |
| 9,060,765 B2 | 6/2015 | Rencher et al. | |
| 9,119,284 B2 | 8/2015 | Sanematsu | |
| 9,144,453 B2 | 9/2015 | Rencher et al. | |
| 9,649,143 B2 | 5/2017 | Konesky et al. | |
| 2004/0116918 A1 | 6/2004 | Konesky | |
| 2005/0118350 A1 * | 6/2005 | Koulik ................. A61B 18/042 427/535 |
| 2005/0187542 A1 | 8/2005 | Auge et al. | |
| 2005/0234442 A1 | 10/2005 | Spears | |
| 2006/0005545 A1 | 1/2006 | Samimy et al. | |
| 2006/0224154 A1 | 10/2006 | Shadduck et al. | |
| 2007/0089795 A1 | 4/2007 | Jacob | |
| 2008/0108985 A1 | 5/2008 | Konesky | |
| 2008/0193329 A1 | 8/2008 | Akishev et al. | |
| 2008/0302767 A1 | 12/2008 | Yamaguchi et al. | |
| 2009/0024122 A1 | 1/2009 | Fischer | |
| 2010/0021340 A1 | 1/2010 | Buske et al. | |
| 2011/0071517 A1 | 3/2011 | Konesky et al. | |
| 2011/0301412 A1 | 12/2011 | Cho | |
| 2012/0065635 A1 | 3/2012 | Konesky | |
| 2012/0116397 A1 * | 5/2012 | Rencher ............... A61B 18/042 606/45 |
| 2012/0172789 A1 | 7/2012 | Fischer et al. | |
| 2014/0005665 A1 | 1/2014 | Konesky et al. | |
| 2014/0316403 A1 | 10/2014 | Konesky et al. | |
| 2014/0341786 A1 | 11/2014 | Konesky | |
| 2015/0132711 A1 | 5/2015 | Mason | |
| 2016/0287310 A1 | 10/2016 | Nettesheim et al. | |
| 2018/0085155 A1 * | 3/2018 | Konesky ............... A61B 18/042 | |

FOREIGN PATENT DOCUMENTS

| | | | |
|---|---|---|---|
| EP | 3765638 A1 | 4/1997 | |
| JP | 2007305845 A | 11/2007 | |
| JP | 2008053661 | 3/2008 | |
| WO | 2006100030 A1 | 9/2006 | |
| WO | WO2007071720 | 6/2007 | |
| WO | WO2011029573 | 3/2011 | |
| WO | 2015059702 A1 | 4/2015 | |
| WO | WO2015059702 | 4/2015 | |
| WO | WO-2015059702 A1 * | 4/2015 | ............ B23K 10/00 |
| WO | WO2015087287 | 6/2015 | |

OTHER PUBLICATIONS

English Translation of Office Action for Chinese Application No. 201680080933.3; dated Jun. 11, 2020; sixteen (16) pages.
European Search Report for European Application No. 16871548.0; dated Jun. 21, 2019; eight (8) pages.
English translation for CN103537245 obtained from the European Patent Office website (www.epo.org) on Jan. 11, 2021, ten (10) pages.
English translation for JP2007305845 obtained from the European Patent Office website (www.epo.org) on Jan. 11, 2021, seventeen (17) pages.
English translation for EP0765638 obtained from the European Patent Office website (www.epo.org) on Jan. 11, 2021, eleven (11) pages.

* cited by examiner

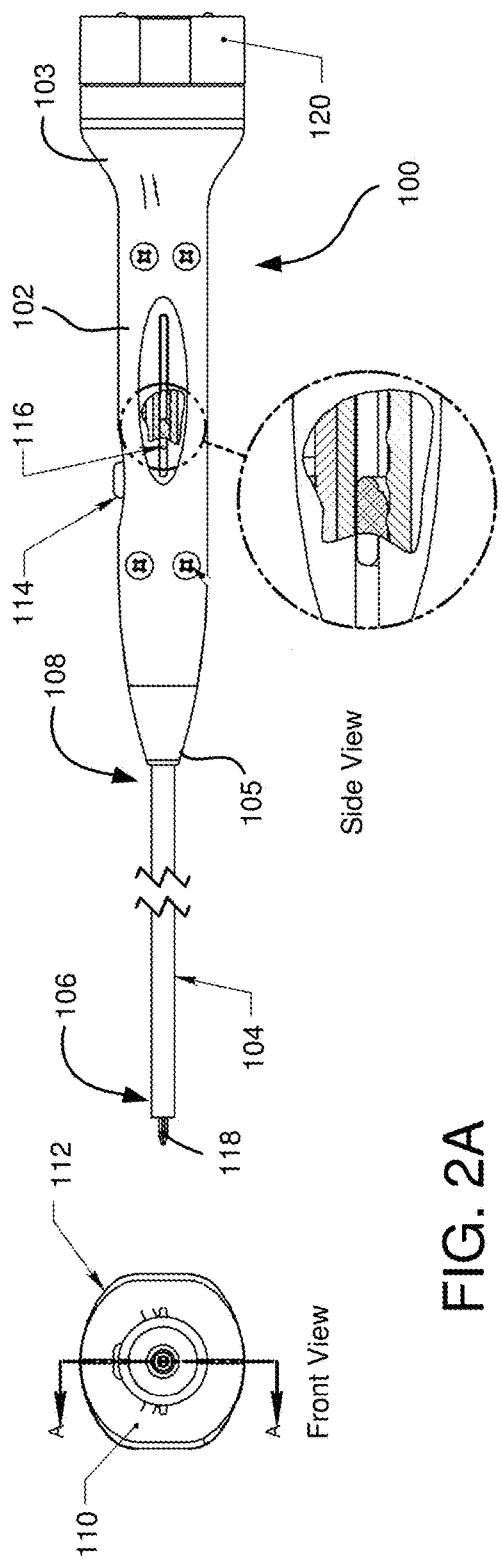
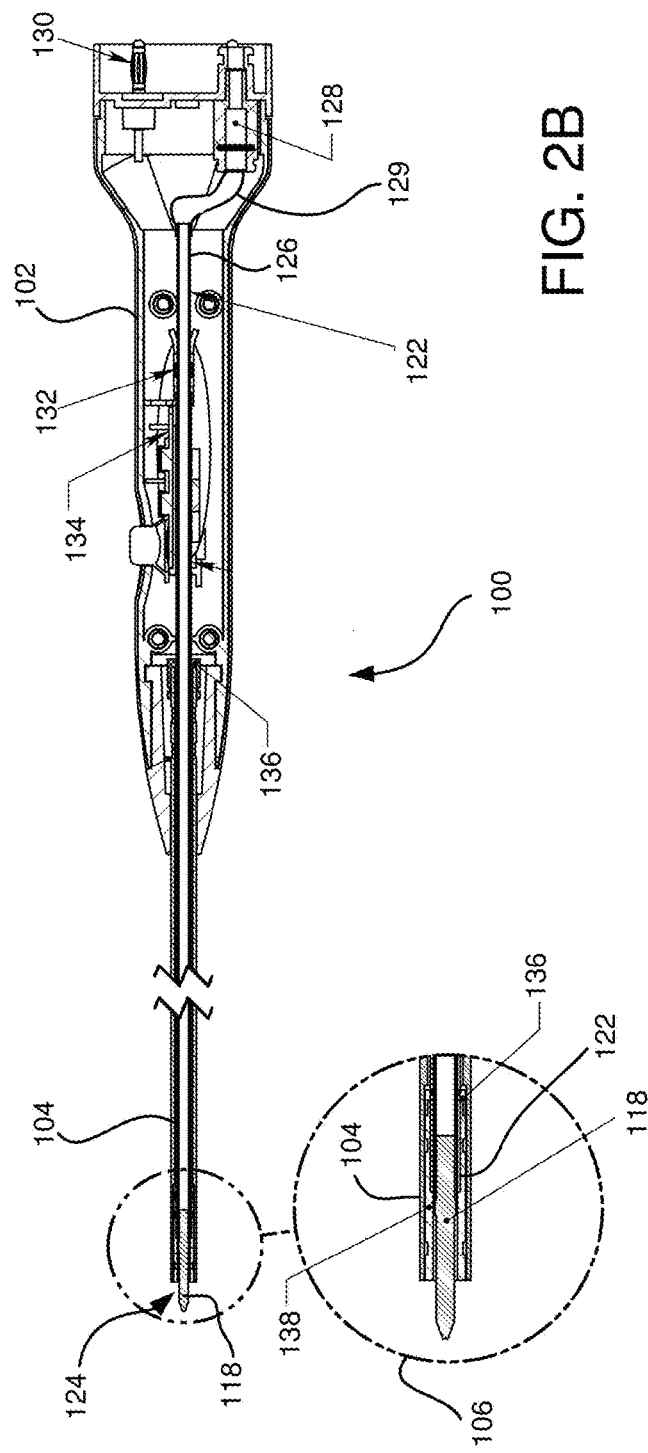
FIG. 2A
FIG. 2B

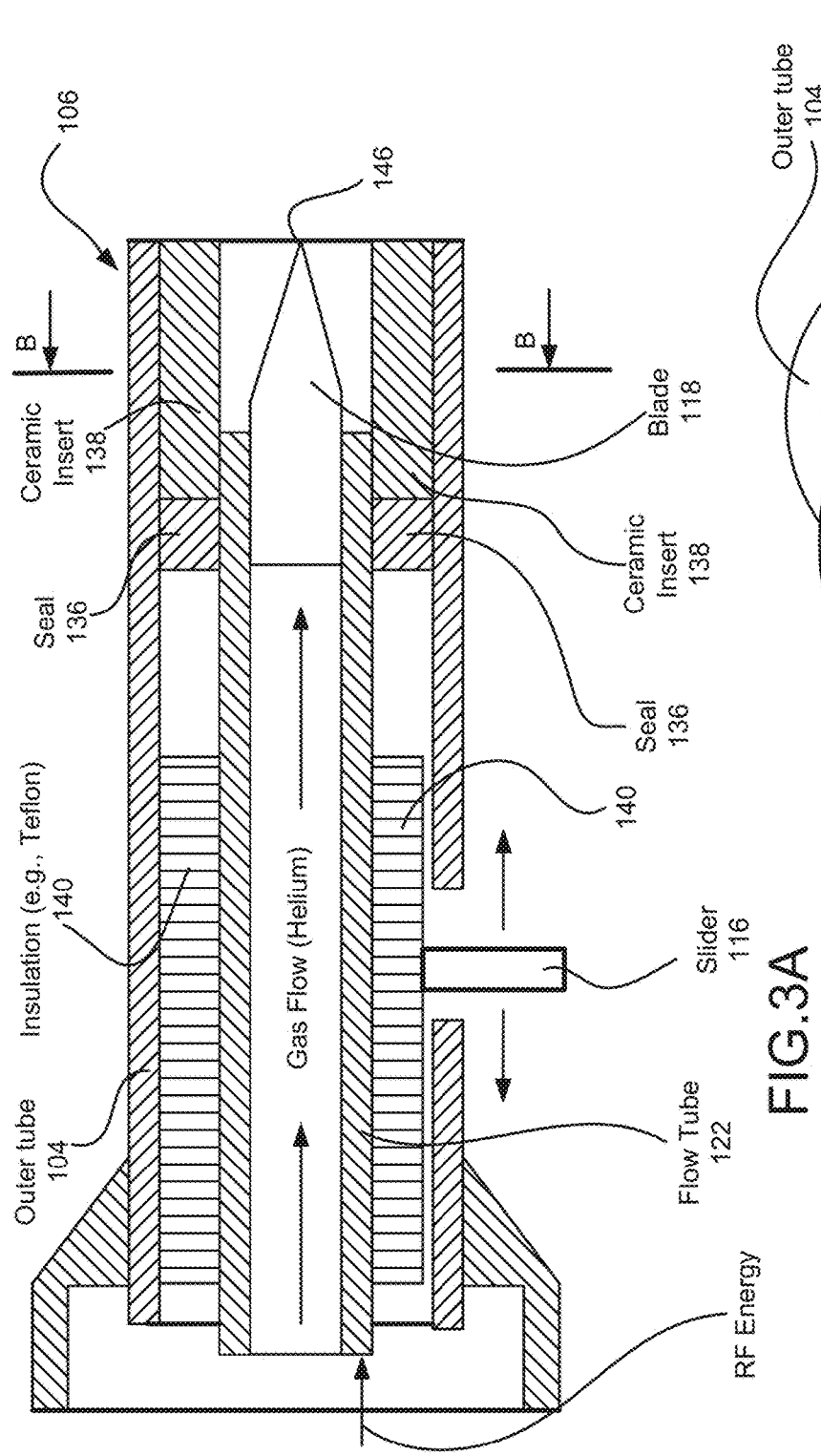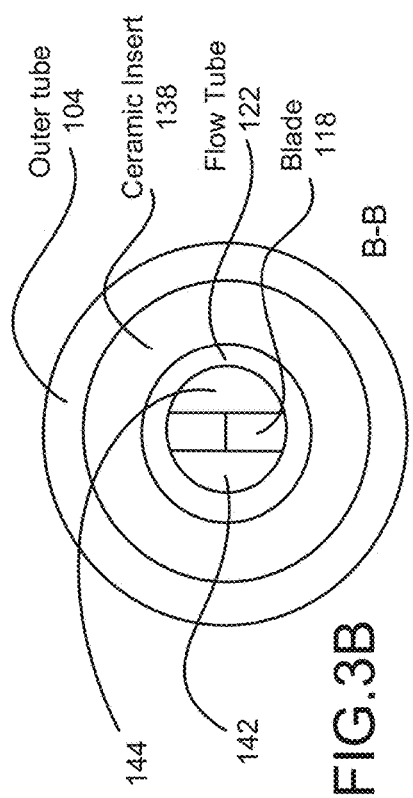

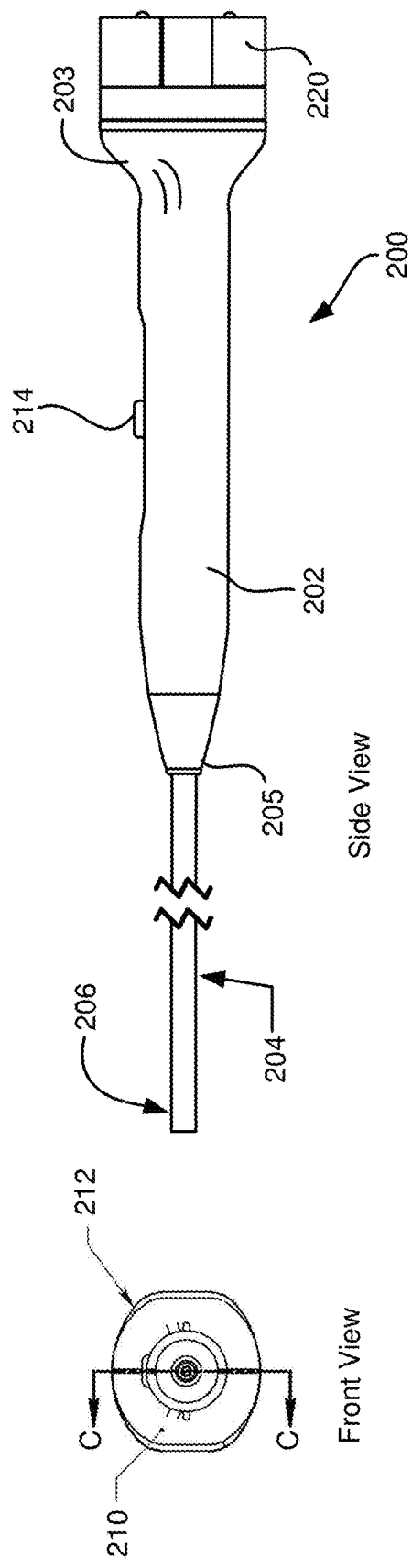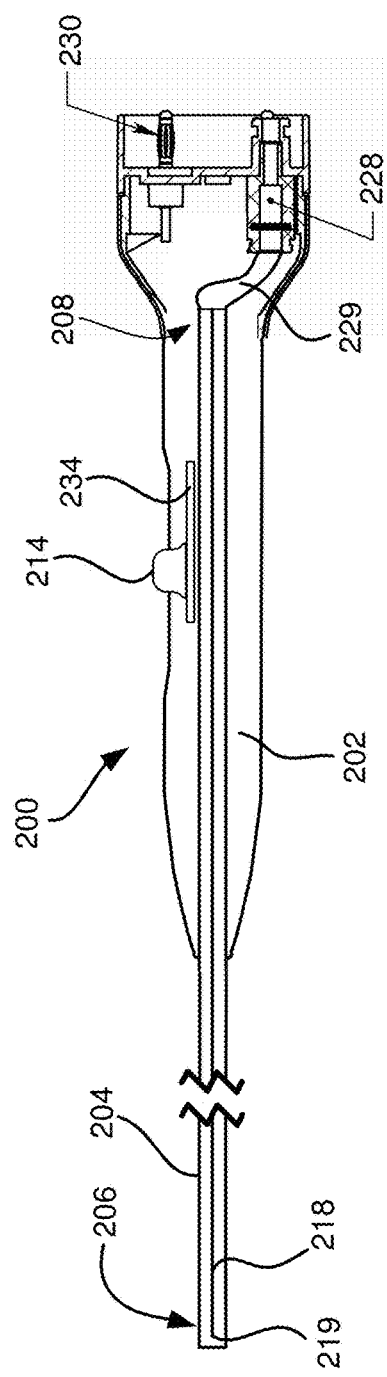
FIG. 5A
Side View
FIG. 5B

SETUP TO VIEW THE PLASMA BEAM
OF A DIRECT DISCHARGE APPLICATOR

DARKENED CLOSE-UP VIEW OF
DIRECT PLASMA BEAM

Comparison of diffusion lengths for small and large diameter tubes.

Use of an Augmenter to improve mixing.

Tilted vanes within the exit nozzle to improve mixing.

Cross-section Views For Both Images
Exit nozzle with advection holes for improved mixing.

MIXING COLD PLASMA BEAM JETS WITH ATMOPSHERE

PRIORITY

This application claims priority to PCT Patent Application No. PCT/US2016/064537, filed Dec. 2, 2016, which claims priority to U.S. Provisional Patent Appl. No. 62/261,914, filed Dec. 2, 2015, entitled "DEVICES, SYSTEMS AND METHODS FOR IMPROVED MIXING OF COLD PLASMA BEAM JETS WITH AMBIENT ATMOSPHERE FOR ENHANCED PRODUCTION OF RADICAL SPECIES", the contents of which are hereby incorporated by reference in its entirety.

BACKGROUND

Field

The present disclosure relates generally to electrosurgery and electrosurgical systems and apparatuses, and more particularly, to devices, systems and methods for improved mixing of cold plasma beam jets with ambient atmosphere for enhanced production of radical species.

Description of the Related Art

High frequency electrical energy has been widely used in surgery and is commonly referred to as electrosurgical energy. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes.

Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. Often, a simple surgical knife is used to excise the tissue in question, followed by the use of a cold plasma applicator for cauterization, sterilization, and hemostasis. Cold plasma beam applicators have been developed for both open and endoscopic procedures.

SUMMARY

Devices, systems and methods for improved mixing of cold plasma beam jets with ambient atmosphere for enhanced production of radical species are provided.

According to one aspect of the present disclosure, an electrosurgical apparatus is provided including a housing having a passage extending therethrough; a gas flow tube having a proximal end and a distal end, the gas flow tube being at least partially disposed in the passage of the housing; and an electrode disposed within the flow tube and configured to be energized to form plasma at the distal end of the gas flow tube when an inert gas flows through the gas flow tube, wherein the distal end of the gas flow tube includes an end effector configured to mix ambient air with the inert gas to increase radical species production in the plasma.

In another aspect, the end effector includes a cylindrical augmenter disposed around the distal end of the gas flow tube, the cylindrical augmenter including a distal end and a proximal end, the distal end and proximal end of the cylindrical augmenter each including an opening, wherein when inert gas flows through the gas flow tube, the cylindrical augmenter is configured to create a Venturi effect to draw ambient air into the proximal opening of the cylindrical augmenter to mix the ambient air with the inert gas.

In a further aspect, the cylindrical augmenter includes at least one first tilted vane disposed on an inner surface of the cylindrical augmenter, the at least one first tilted vane configured to impart a tangential velocity component to the ambient air drawn into the proximal opening of the cylindrical augmenter.

In one aspect, the gas flow tube includes at least one second tilted vane disposed on an inner surface of the gas flow tube.

In another aspect, the at least one first tilted vane is tilted in a different direction than the at least one second tilted vane.

In yet another aspect, the end effector includes at least one tilted vane disposed on an inner surface of the gas flow tube, the at least one tilted vane configured to impart a tangential velocity component to the inert gas.

In a further aspect, the end effector includes at least one advection aperture in a distal portion of a wall of the gas flow tube.

In another aspect, the end effector includes at least one deflection hood coupled to the gas flow tube, the at least one deflection hood configured to at least partially cover the at least one advection aperture.

In still another aspect, the end effector includes at least one tilted vane disposed on an inner surface of the gas flow tube.

In yet another aspect, the end effector includes a cylindrical augmenter disposed around the distal end of the gas flow tube, the cylindrical augmenter includes at least two tilted vanes diametrically opposed on an inner surface of the cylindrical augmenter to impart a tangential velocity component to the ambient air drawn into the cylindrical augmenter.

According to another aspect of the present disclosure, an electrosurgical apparatus is provided including a housing having a passage extending therethrough, the housing having a proximal end and a distal end; an electrically conducting tube having a proximal end and a distal end, the electrically conducting tube at least partially disposed in the passage of the housing; an insulating outer tube having a proximal end and a distal end, the outer tube disposed around the electrically conducting tube with the proximal end of the outer tube coupled to the distal end of the housing, the electrically conducting tube being movable along a longitudinal axis of the housing and outer tube; and an electrode coupled to the distal end of the electrically conducting tube, wherein, in a first position of the electrically conducting tube, the electrode extends beyond the distal end of the outer tube and, in a second position of the electrically conducting tube, the electrode is retracted within the outer tube and is energized via the electrically conducting tube to form plasma when an inert gas flows through the electrically conducting tube, wherein the distal end of the insulating outer tube includes an end effector configured to mix ambient air with the inert gas to increase radical species production in the plasma.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A is a schematic diagram of an electrosurgical apparatus in accordance with an embodiment of the present disclosure;

FIG. 2B is a cross sectional view of the electrosurgical apparatus shown in FIG. 2A taken along line A-A;

FIG. 3A is an enlarged cross sectional view of the electrosurgical apparatus in accordance with an embodiment of the present disclosure;

FIG. 3B illustrates a front view of the electrosurgical apparatus shown in FIG. 3A taken along line B-B;

FIG. 5A illustrates an electrosurgical apparatus having a centrally mounted electrode disposed in a gas flow tube in accordance with an embodiment of the present disclosure;

FIG. 5B is a cross sectional view of the electrosurgical apparatus shown in FIG. 5A taken along line C-C in accordance with an embodiment of the present disclosure;

Figure 1:
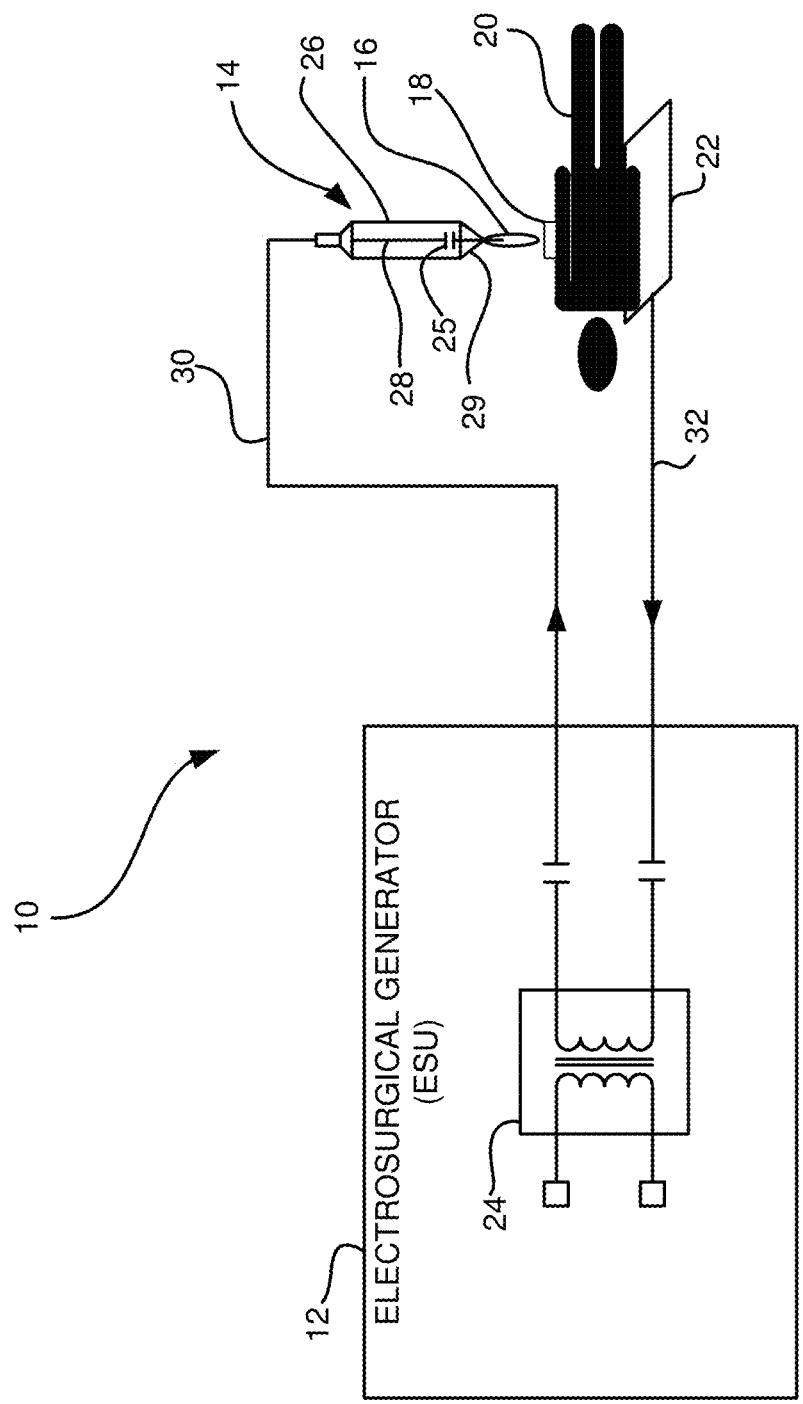
FIG. 1 is an illustration of an exemplary monopolar electrosurgical system in accordance with an embodiment of the present disclosure.

It should be understood that the drawing(s) is for purposes of illustrating the concepts of the disclosure and is not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

The effects of medical cold plasma jet beams can broadly be grouped into two categories. The first category includes prompt effects, typically employed in surgical procedures. These involve coagulation, vessel sealing and hemostasis, resection and bulk tissue removal through ablation, and infectious agent destruction. The prompt effects derive from electron and ion bombardment, high electric fields, localized thermal effects, and a small amount of ultra-violet light production, which act either individually or in concert.

The second category relates to delayed and/or prolonged medical and biomedical effects. They include continued infectious agent destruction and inactivation, stimulated wound healing, cancer treatment, and immune system recruitment. These effects derive from the production of radical species through the interaction of the plasma beam with the components of ambient air, including oxygen, nitrogen, and water vapor. The radical species produced include reactive oxygen species (ROS), reactive nitrogen species (RNS) and reactive oxy-nitrogen species (RONS).

These reactive species become dissolved into the aqueous component of tissue and/or the inter and intra cellular fluids to which the cold plasma beam is applied. They produce soluble species such as nitric oxide (NO) and higher oxides of nitrogen (NXOY), hydroxyl radical (OH—), and hydrogen peroxide ($H_2O_2$). The dissolved radical species provide both delayed and prolonged biological effects, long after exposure to the plasma beam itself has ceased. Note that the effects of these soluble radical species can be expressed a considerable distance away from the plasma beam application site due to their solution mobility. Plasma Activated Media (PAM) can also be prepared by the action of a plasma beam on an aqueous medium, and the prepared PAM can then be used separately and independently of the plasma beam.

The production rate of radical species by the plasma beam can be enhanced by pre-mixing various atmospheric components into the plasma beam carrier gas, although this requires a specially prepared premix gas supply. An alternative approach would be to enhance the interaction of the plasma beam with the surrounding ambient air. The reactive species are produced through collisions, charge exchange, and high electric fields, present in the plasma beam, with the ambient air immediately surrounding the plasma beam. The greater the degrees of interaction of the ambient air with the periphery of the plasma beam, the greater the rate of radical species production.

There are limits to the degree of mixing of ambient air with the carrier gas of the plasma beam. For example, too much turbulence at the outer boundary of the plasma beam jet and the ambient air can distort the plasma beam, causing loss of beam structural definition, and limiting precise application of the beam to a target site. Also, too much dilution of the plasma beam carrier gas, typically helium, argon, or a mixture of the two, with air will raise the breakdown voltage. This may result in a shorter plasma beam. Since the mixing of the ambient air and the plasma beam occurs along the length of the discharge, and this process produces the desired radical species, there may be a point of diminishing returns. In other words, a shorter beam which is highly mixed with ambient air may produce less radical species than a longer beam that is optimally mixed.

Atmospheric pressure cold plasma discharge beam jets are generally formed by one of two mechanisms. The first is referred to as a "local" discharge, where the primary plasma discharge is confined to the plasma applicator handpiece. The flowing carrier gas draws out an afterglow, which forms the visible beam emerging from the exit nozzle tip of the applicator handpiece. Such local discharge applicators typically have a ground ring around the outer periphery of the exit nozzle tip and complete the plasma discharge circuit within the handpiece.

The second type of cold plasma applicator has a centrally mounted electrode wire positioned down the longitudinal axis of an insulating tube. An exemplary cold plasma applicator having a centrally mounted electrode wire is shown and described in commonly owned U.S. Pat. No. 7,316,682 to Konesky, the details of which will be described below in relation to FIGS. 1, 5A and 5B. The wire may also be flattened into a cutting blade which, when retracted into the insulating tube, serves as an electrode. An exemplary cold plasma applicator having an electrode configured as a cutting blade is shown and described in commonly owned U.S. Pat. No. 9,060,765 to Rencher et al., the details of which will be described below in relation to FIGS. 2A through 4. Regardless of the applicator configuration, the electrode is held at high voltage and high frequency, typically from a few hundred to a few thousand volts, and several kilohertz to several megahertz, respectively. Inert carrier gas flowing through the tube, and over the electrode, produces a luminous discharge path from the tip of the electrode to the target application site. The discharge path occurs directly from the exit tip of the applicator handpiece to the target application site, so it is said to be a "direct" discharge applicator.

FIG. 1 shows an exemplary monopolar electrosurgical system generally indicated as 10 comprising an electrosurgical generator (ESU) generally indicated as 12 to generate power for the electrosurgical apparatus 10 and a cold plasma applicator or generator having a centrally mounted electrode wire generally indicated as 14 to generate and apply a plasma stream or beam 16 to a surgical site or target area 18 on a patient 20 resting on a conductive plate or support surface 22. The electrosurgical generator 12 includes a transformer generally indicated as 24, including a primary winding and a secondary winding, coupled to an electrical source (not shown) to provide high frequency electrical energy to the cold plasma applicator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The cold plasma applicator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary winding of the transformer 24 through an active conductor 30 to the electrode 28 (collectively active electrode) in the handpiece 26 to create the plasma stream 16 for application to the surgical site 18 on the patient 20. Furthermore, a current limiting capacitor 25 is provided in series with the electrode 28 to limit the amount of current being delivered to the patient 20.

The return path to the electrosurgical generator 12 is through the tissue and body fluid of the patient 20, the conductor plate or support member 22 and a return conductor 32 (collectively return electrode) to the secondary winding of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the cold plasma applicator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

It is to be appreciated that transformer 24 may be disposed in the cold plasma applicator handpiece 26, as will be described in various embodiments below. In this configuration, other transformers may be provided in the generator 12 for providing a proper voltage and current to the transformer in the handpiece, e.g., a step-down transformer, a step-up transformer or any combination thereof.

Referring to FIG. 2A, a cold plasma applicator having an electrode wire configured as a cutting blade in accordance with the present disclosure is illustrated. Such a cold plasma applicator is described in commonly owned U.S. Pat. No. 9,060,765 to Rencher et al., the contents of which are hereby incorporated by reference in its entirety. Generally, the applicator 100 includes a housing 102 having a proximal end 103 and a distal end 105 and a tube 104 having an open distal end 106 and a proximal end 108 coupled to the distal end 105 of the housing 102. The housing 102 includes a right side housing 110 and left side housing 112, and further includes provisions for a button 114 and slider 116. Activation of the slider 116 will expose a blade 118 at the open distal end 106 of the tube 104. Activation of the button 114 will apply electrosurgical energy to the blade 118 and, in certain embodiments, enable gas flow through the flow tube 122, as will be described in detail below. It is to be appreciated that housing 102 is configured to be held by a user to use and manipulate applicator 100 in surgical applications.

Additionally, a transformer 120 is provided on the proximal end 103 of the housing 102 for coupling a source of radio frequency (RF) energy to the applicator 100. By providing the transformer 120 in the applicator 100 (as opposed to locating the transformer in the electrosurgical generator), power for the applicator 100 develops from higher voltage and lower current than that required when the transformer is located remotely in the generator, which results in lower thermalization effects. In contrast, a transformer back in the generator produces applicator power at a lower voltage, higher current with greater thermalization effects. Therefore, by providing the transformer 120 in apparatus 100, collateral damage to tissue at the operative site is minimized. However, it is to be appreciated that the present disclosure contemplates embodiments with the transformer disposed in the handpiece or in the generator depending on the procedure or desired effects.

A cross section view along line A-A of the applicator 100 is shown in FIG. 2B. Disposed within the housing 102 and tube 104 is flow tube 122 which runs along the longitudinal axis of the apparatus 100. On a distal end 124 of the flow tube 122, the blade 118 is retained within the flow tube 122. A proximal end 126 of the flow tube 122 is coupled to a source of gas (not shown) via a tube connector 128 and flexible tubing 129. The proximal end 126 of the flow tube 122 is also coupled to a source of RF energy via plug 130 which, in one embodiment, couples to transformer 120 and, in another embodiment, couples to a transformer disposed in an electrosurgical generator. The flow tube 122 is made of an electrically conducting material, preferably stainless steel, as to conduct the RF energy to the blade 118 when being employed for plasma applications or electrosurgical cutting as will be described below. The outer tube 104 is constructed from non-conductive material, e.g., Lestran. The slider 116, which extends through an aperture in the housing 102, is coupled to the flow tube 122 via a retaining collar 132. A printed circuit board (PCB) 134 is disposed in the housing 102 and controls the application of the RF energy from the transformer 120 via the button 114.

An enlarged view of the distal end 106 of the outer tube 104 is also illustrated in FIG. 2B. Here, the blade 118 is coupled to the flow tube 122 which is held in place in the outer tube 104 by at least one seal 136. The at least one seal 136 prevents backflow of gas into tube 104 and housing 102. A cylindrical ceramic insert 138 is disposed in the distal end of the outer tube 104 to maintain the blade along the longitudinal axis of the apparatus or applicator 100 and provide structural support during mechanical cutting when the blade is exposed beyond the distal end 106 of the outer tube 104.

The operational aspect of the apparatus or applicator 100 will now be described in relation to FIGS. 3A and 3B, where FIG. 3A shows an enlarged cross section of the apparatus and FIG. 3B illustrates a front view of the apparatus.

Referring to FIG. 3A, the flow tube 122 is disposed in the outer tube 104 with a cylindrical insulator 140 disposed around the flow tube 122. Slider 116 is coupled to the insulator 140 (or in other embodiments to the flow tube 122) and is employed to extend and retract the blade 118 by sliding the flow tube 122. At the distal end 106 of the outer tube 104, the annular or ring shaped seal 136 and cylindrical ceramic insert 138 are disposed about the flow tube 122. As can be seen in FIG. 3B, the generally planar blade 118 is coupled to an inner circumference of the cylindrical flow tube 122 such that two gas passageways 142, 144 are formed on the both sides of the blade 118. As gas flows from the proximal end 103 of the housing through the flow tube 122, the gas will pass over the blade 118 out the distal end of the outer tube 104.

When the blade is in the retracted position as shown in FIG. 3A, the applicator 100 is suitable for generating plasma. In the retracted position, RF energy is conducted to a tip 146 of the blade 118 from an electrosurgical generator (not shown) via the flow tube 122. An inert gas, such as helium or argon, is then supplied to the flow tube 122 from either the electrosurgical generator or an external gas source via tube connector 128. As the inert gas flows over the sharp point 146 of the blade 118 held at high voltage and high frequency, a cold plasma beam is generated.

Figure 4:
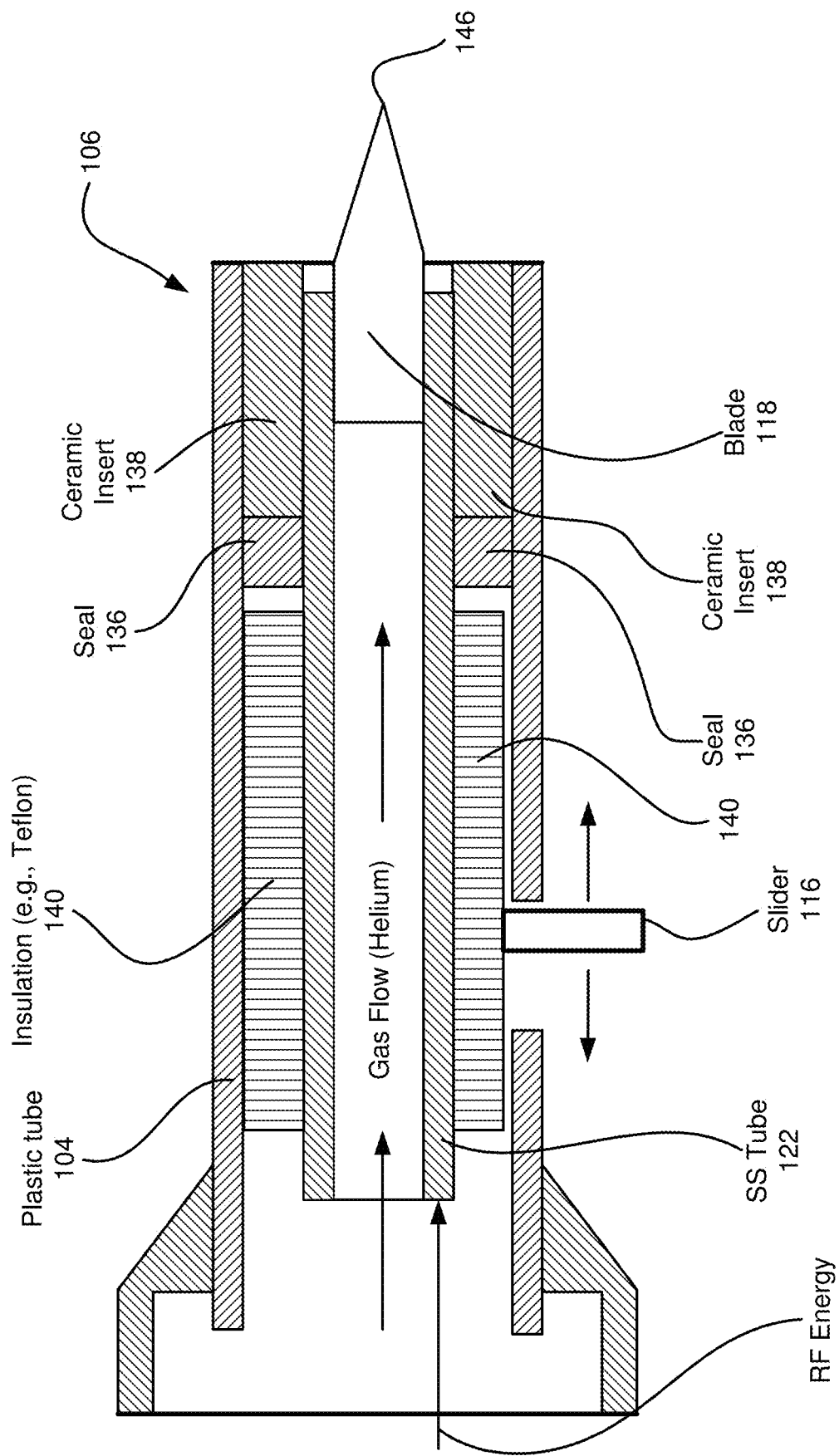
FIG. 4 is an enlarged cross sectional view of the electrosurgical apparatus shown in FIG. 3A with a blade extended.

Referring to FIG. 4, the blade 118 is advanced, via slider 116, so the tip 146 is extended past the distal end 106 of the outer tube 104. In this state, the blade 118 may be used for two cutting modes: mechanical cutting and electrosurgical cutting. In the mechanical cutting mode, RF or electrosurgical energy is not applied to the flow tube 122 or blade 118, and therefore, the blade 118 is in a de-energized state. In this mode, the blade 118 can be used excise tissue via mechanical cutting, i.e., similar to a conventional scalpel where the blade makes contact with the tissue. After the tissue is removed, the blade 118 may be retracted via the slider 116 and electrosurgical energy and gas may be applied via button 114 to generate a cold plasma beam for cauterization, sterilization and/or hemostasis of the operative patient site.

Referring to FIG. 5A, a cold plasma applicator having a centrally mounted electrode, e.g., a wire electrode, disposed in a gas flow tube in accordance with the present disclosure is illustrated. Generally, the applicator 200 includes a housing 202 having a proximal end 203 and a distal end 205 and a gas flow tube 204 having an open distal end 206 and a proximal end 208 (shown in FIG. 5B) coupled to a source of gas via a tube internal to housing 202, as will be described below. It is to be appreciated that the gas flow tube is at least partially disposed in a passage extending through the housing 202. Furthermore, it is to be appreciated that in this embodiment gas flow tube 204 may be made of an insulating material or other non-conducting material.

The housing 202 includes a right side housing 210 and left side housing 212, and further includes provisions for a button 214. Activation of the button 214 will apply electrosurgical energy to the electrode 218 (shown in FIG. 5B) and, in certain embodiments, enable gas flow through the gas flow tube 204, as will be described in detail below. Additionally, in one embodiment, a transformer 220 is provided on the proximal end 203 of the housing 202 for coupling a source of radio frequency (RF) energy to the applicator 200. In another embodiment, the transformer is disposed in an electrosurgical generator and the proximal end 203 includes a connection 230 for receiving the RF energy from the generator. It is to be appreciated that housing 202 is configured to be held by a user to use and manipulate applicator 200 in surgical applications.

A cross section view along line C-C of the applicator 202 is shown in FIG. 5B, where certain components have been removed for clarity. Disposed within a passage of the housing 202 is gas flow tube 204 which runs along the longitudinal axis of the apparatus 200. Electrode 218 is disposed within gas flow tube 204. In one embodiment, electrode 218 is an electrically conducting wire that is centrally mounted within gas flow tube 204, such that a distal end tip 219 of electrode 218 is recessed within open distal end 206 of gas flow tube 204. Electrode 218 extends along the longitudinal axis within gas flow tube 204 from distal end 206 of gas flow tube 204 to proximal end 208 of gas flow tube 204. A proximal end 208 of the gas flow tube 204 is coupled to a source of gas via a tube connector 228 and flexible tubing 229. Although not shown, electrode 218 is coupled to a source of RF energy via plug 230, which couples to transformer 220 (or to a transformer in the electrosurgical generator). A printed circuit board (PCB) 234 is disposed in the housing 202 and controls the application of the RF energy to electrode 218 via the button 214.

Although in each of the above described embodiments relating to applicators 100 and 200, housings 102, 202 are shown as having a generally straight cylindrical shape to be gripped by a user, it is to be appreciated that in other embodiments housings 102, 202 may be configured in other shapes to be gripped differently by a user. For example, in another embodiment, housings 102, 202 may be configured in a pistol-grip configuration. In this embodiment, housings 102, 202 include a grip extending perpendicularly from the longitudinal axis of housing 102 or flow tubes 122, 204, where the grip is configured to be grasped or held by a user. The grip may include a trigger and/or one or more buttons that may be assigned the functions of buttons 114, 214, and slider 116.

Furthermore, although transformers 120, 220 are shown disposed on the proximal ends 103, 203 of housings 102, 202, it is to be appreciated that in other embodiments applicators 100, 200 may be configured such that transformers 120, 220 are disposed external to applicators 100, 200. For example, in one embodiment, transformers 120, 220 may be removed from applicators 100, 200 and applicator 100, 200 may be coupled to an electrosurgical generator, such as, ESU 12, which includes transformer 24, to receive RF energy to be provided to blade 118 or electrode 218. It is to be appreciated that transformer 120, 220 may be disposed in ESU 12 as needed to supply the appropriate RF energy to the applicator.

Figure 6A:
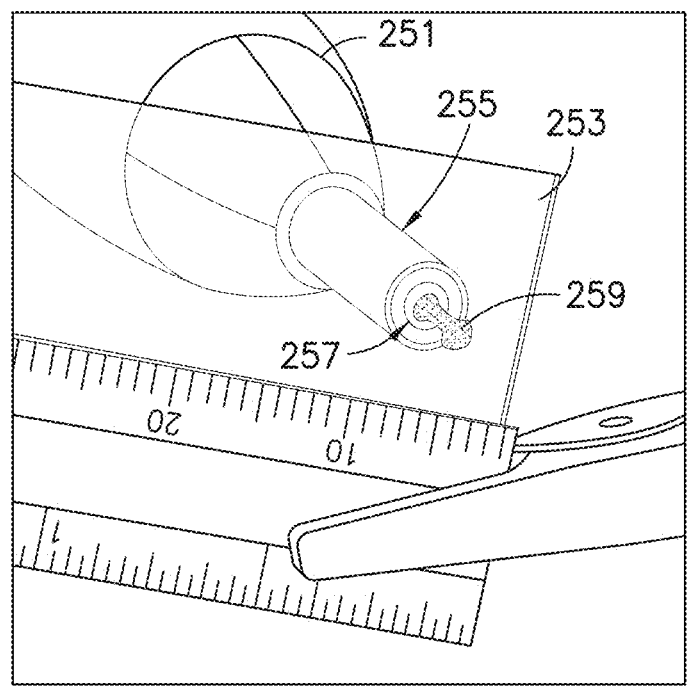
FIG. 6A illustrates an exemplary setup to view a plasma beam of a direct discharge applicator in accordance with an embodiment of the present disclosure.
Figure 6B:
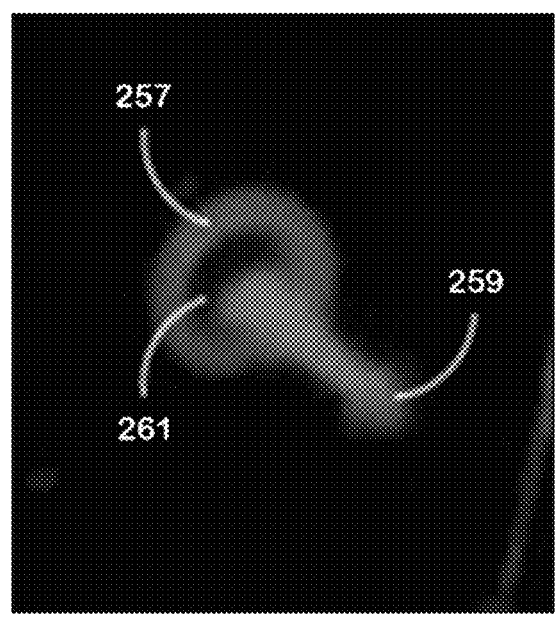
FIG. 6B illustrates a darkened close-up view of the direct plasma beam shown in FIG. 6A.

In both types of the cold plasma applicators described above (e.g., applicators 14 and 200, which include a centrally mounted electrode wire, and applicator 100, which includes a retractable blade electrode), only a small fraction of the inert carrier gas is ionized, typically between one part in a thousand to one part in a million. The vast majority of the carrier gas flow is not ionized, and the actual beam discharge path forms an interior core of the overall jet beam, with the un-ionized gas forming a column or sheath around the jet beam. This effect is illustrated in FIGS. 6A and 6B. Here, a direct-type applicator 251 (as described above in relation to FIGS. 2A through 4) is shown with a retracted flat surgical blade that serves as an electrode. A glass slide 253 coated with transparent indium tin oxide (ITO) acts as the target application site. The conductive ITO is grounded and affords a view upward into the beam axis of the plasma beam 259 emitted by applicator 251. The overall setup to view the plasma beam is shown in FIG. 6A, and a darkened close-up view of the direct plasma beam is shown in FIG. 6B.

The inert carrier gas flowing from the exit nozzle 255 disposed at the distal end of a direct discharge applicator handpiece 251 occupies the entire inside diameter 257 of the nozzle 255. However, it can be seen in FIG. 6B that the actual plasma discharge beam 259 occupies only an inner part of that diameter. In other words, the luminous discharge beam is surrounded by a sheath 261 of un-ionized carrier gas. This presents a diffusion barrier through which ambient air molecules must pass through to reach the plasma beam 259, and then interact with the plasma beam 259 to generate radical species. All things being equal, the larger the inside diameter 257 of the applicator exit nozzle 255 with respect to the plasma discharge beam diameter, the lower the rate of radical species production, as illustrated in FIG. 6C.

Figure 6C:
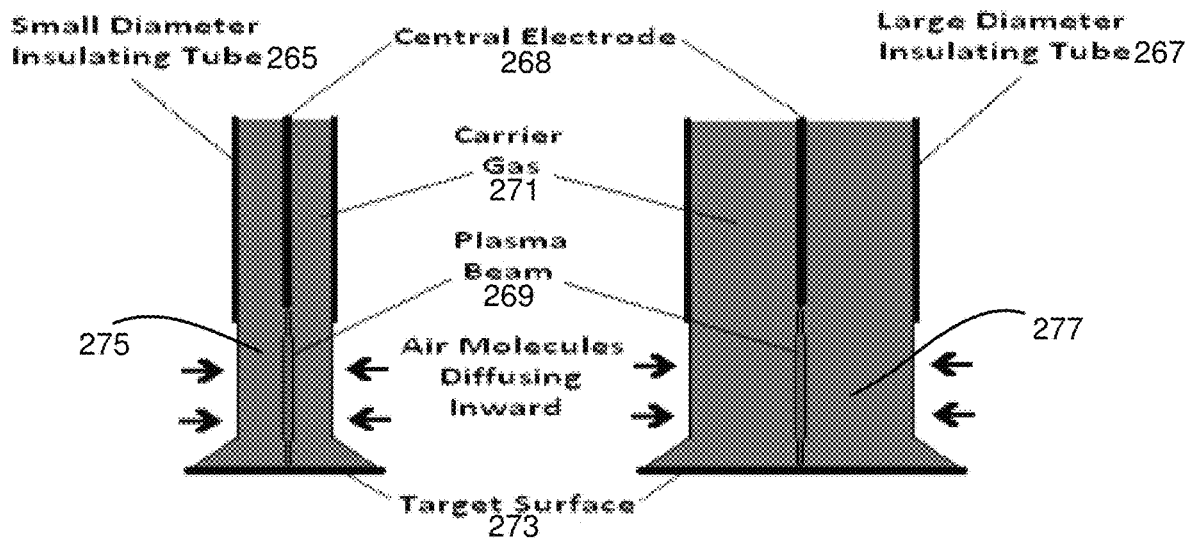
FIG. 6C illustrates a comparison of diffusion lengths for small and large diameter tubes.

Referring to FIG. 6C, a small diameter insulating tube applicator 265 is shown in side by side comparison with a large diameter insulating tube applicator 267. The plasma beam 269 is shown being generated from the electrode 268 as carrier gas 271 passes through the corresponding tube to the target surface 273. A sheath or column of carrier gas surrounds the plasma beam 269, where column 275 surrounds plasma beam 269 in the small diameter insulating tube applicator 265 and column 277 surrounds plasma beam 269 in the large diameter insulating tube applicator 267. As can be seen from FIG. 6C, the larger the inside diameter of the applicator exit nozzle (e.g., the distal end of the insulating tube) the thicker the sheath or column of carrier gas surrounding the plasma discharge beam (i.e., column 277 is larger than column 275) thereby impeding the ambient air from reaching the plasma beam and reducing the rate of radical species production.

It should be noted that, for a fair comparison, equal nozzle carrier gas flow velocities should be considered for different diameter tubes, rather than equal flow rates. If equal flow rates are used for a comparison, then the larger diameter tube will have a substantially lower flow velocity due to the larger cross-sectional area. This will allow more time for ambient air to diffuse in toward the plasma beam, and decrease the apparent difference in radical species production rates.

Ideally, the exit nozzle of the gas flow tube should be made as small as possible to maximize radical species production. However, there are other considerations. In many surgical procedures, the flowing gas also serves to carry away waste heat from the operative site, reducing collateral damage to surrounding tissue. This is especially true when helium is used as the carrier gas, due to its high thermal conductivity. Therefore, a tradeoff must be made between radical species production maximization, and the need to minimize operative site collateral damage. Also, a limit is reached when the tube diameter is made so small that for a given minimum flow rate, turbulence sets in from the high gas velocities. This has negative effects on beam stability and the ability to accurately point the beam to a given target site.

An alternate approach to enhancing radical species production is to improve the mixing of ambient air into the carrier gas stream surrounding the plasma discharge, while still not sacrificing beam stability. This can take two approaches, both of which rely on modifying the often laminar flow boundary between the carrier gas column as it exits the nozzle at the distal end of the carrier gas flow tube, and the surrounding ambient air. By making this boundary non-laminar, mixing is improved. As will be described below, these approaches may be incorporated in applicators 14, 100, and 200, described above, by including an end effector in a distal portion of each of the applicators (e.g., fluid flow housing 29, distal end 106 of tube 104, and/or distal end 206 of tube 204) to increase the production of radical species in accordance with the present disclosure. It is to be appreciated that the end effector may be a separate component or device disposed on the distal end of the applicator or may also encompass design configurations incorporated into the components of the applicator such as, but not limited to, the gas flow tubes, the insulating outer tubes, etc., as will be described in more detail below.

Figure 7:
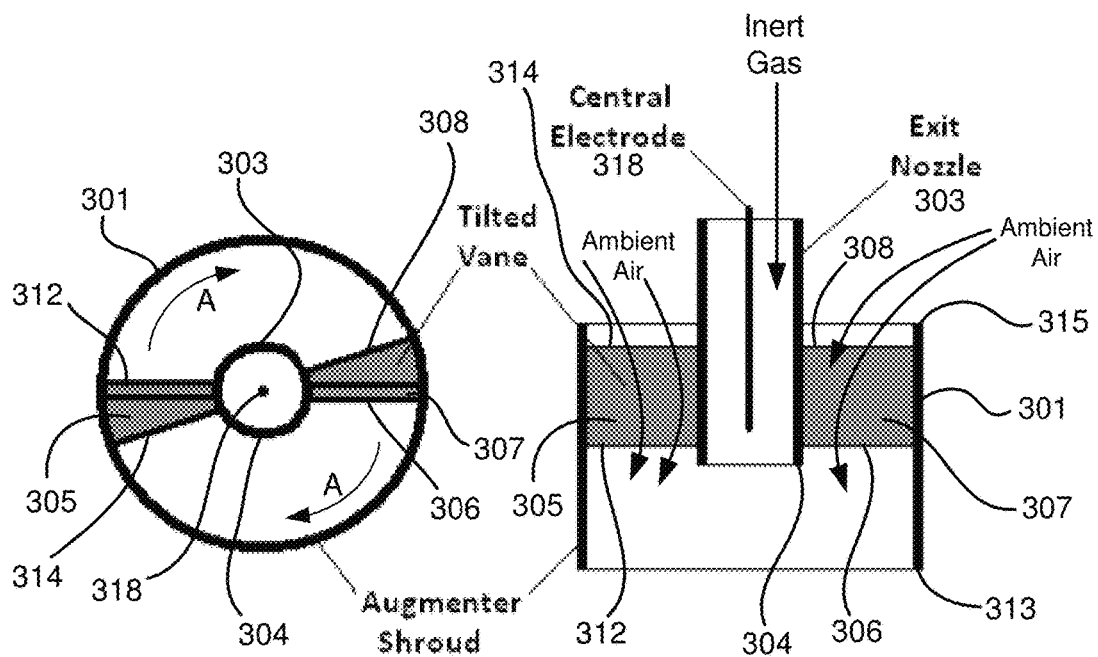
FIG. 7 illustrates use of an augmenter on a cold plasma beam applicator to improve mixing of ambient air and a carrier gas in accordance with an embodiment of the present disclosure.

One approach is to induce a tangential flow velocity component to the surrounding ambient air, or, in other words, to swirl the air around the inert gas column, thereby enhancing mixing. While this can be done with the addition of auxiliary coaxial flow tubes, and associated additional gas (air) feed lines, a simpler approach is to rely on the flow velocity of the carrier gas column to induce or "augment" the flow of the surrounding ambient air, as illustrated in FIG. 7. A generally cylindrical augmenter 301 acting as an end effector for an applicator is disposed on the exit nozzle 303 (which houses electrode 318) or a distal end of the flow tube of an applicator, e.g., the distal end of the fluid flow housing 29 as shown in FIG. 1 or distal end 106 of tube 104 of applicator 100 as shown in FIGS. 2A and 2B or distal end 206 of applicator 200 as shown in FIGS. 5A and 5B. In one embodiment, the end effector or cylindrical augmenter 301 includes tilted vanes 305, 307.

As seen in the cross-sectional view of FIG. 7, cylindrical augmenter or end effector 301 includes a distal end 313 and a proximal end 315, where each of ends 313, 315 include an opening. Cylindrical augmenter 301 is disposed over the distal end 304 of exit nozzle 303, such that, distal end 304 of exit nozzle 303 is recessed within the interior of cylindrical augmenter 301.

As seen in the front view of FIG. 7 (i.e., looking into the distal end of the applicator), tilted vane 305 includes a first portion 312 and a second portion 314, where the first portion 312 is tilted relative to the second portion 314. Tilted vane 307 includes first portion 306 and second portion 308, where first portion 306 is tilted relative to the second portion 308. In one embodiment, tilted vanes 305, 307 are disposed in the annular space between the augmenter 301 and the exit nozzle 303, such that, tilted vanes 305, 307 are each coupled to an inner surface of the wall of cylindrical augmenter 301 and the outer surface of the wall of exit nozzle 303.

Cylindrical augmenter 301 and tilted vanes 305, 307 are configured such that, when inert carrier gas exits the distal end 304 of exit nozzle 303, the cylindrical augmenter 301 creates a Venturi effect to draw ambient air through the opening in the proximal end 315 of cylindrical augmenter 301, where the ambient air that is drawn into the interior of the cylindrical augmenter 301 is mixed with the inert carrier gas exiting the distal end 304 of exit nozzle 303. When the ambient air is drawn into the interior of the cylindrical augmenter 301, the tilted vanes 305, 307 are configured to impart a tangential velocity component (denoted by letter A in the front view shown in FIG. 7) to the ambient air drawn through the augmenter 301.

It is to be appreciated that although two tilted vanes are shown, the number of vanes may be less than two or more than two. Furthermore, it is to be appreciated that although tilted vanes 305, 307 are shown in diametrically opposed positions in the front view of FIG. 7, tilted vanes 305, 307 may be placed in other positions relative to each other within the annular space between cylindrical augmenter 301 and exit nozzle 303.

In some embodiments, cylindrical augmenter 301 and tilted vanes 305, 307 may be included as an end effector in applicators 100, 200 described above. For example, cylindrical augmenter 301 may be disposed over the distal end 106 of outer tube 104, where tilted vanes 305, 307 are each coupled to the inner surface of the wall of cylindrical augmenter 301 and the outer surface of the wall of outer tube 104. As another example, cylindrical augmenter 301 may be disposed over the distal end 206 of gas flow tube 204, where tilted vanes 305, 307 are each coupled to the inner surface of the wall of cylindrical augmenter 301 and the outer surface of the wall of gas flow tube 204. In this way, when cylindrical augmenter 301 is included as an end effector on the distal ends 106, 206 of tubes 104, 204 and inert carrier gas is provided through each of tubes 104, 204 and exits the distal ends 106, 206 of each of the tubes 104, 106, the cylindrical augmenter 301 is configured to draw in ambient air (through the opening in proximal end 315) into the interior of cylindrical augmenter 301. Furthermore, tilted vanes 305, 307 are configured to impart a tangential velocity component to the ambient air that is drawn in to the interior of cylindrical augmenter 301 to mix the ambient air with the inert carrier gas exiting distal ends 106, 206 of tubes 104, 204 to increase production of radical species.

An alternate approach is to configure the end effector of an applicator, such as applicators 14, 100, 200, to induce a tangential velocity component to the carrier gas column as opposed to the ambient air. For example, referring to FIG. 8, a front view and a cross-section view of an exit nozzle 403 of an applicator, such as any one of applicators 14, 100, 200, is shown in accordance with the present disclosure. In the embodiment shown in FIG. 8, the end effector of the applicator includes tilted vanes 405, 407. In this embodiment, tilted vanes 405, 407 are placed inside the exit nozzle 403 which houses electrode 418. The tilted vanes 405, 407 each include a first portion and a second portion, where tilted vane 405 includes first portion 412 that is tilted relative to second portion 414 and tilted vane 407 include first portion 406 that is tilted relative to second portion 408. In one embodiment, tilted vanes 405, 407 are coupled to an inner surface of the wall of exit nozzle 403.

Figure 8:
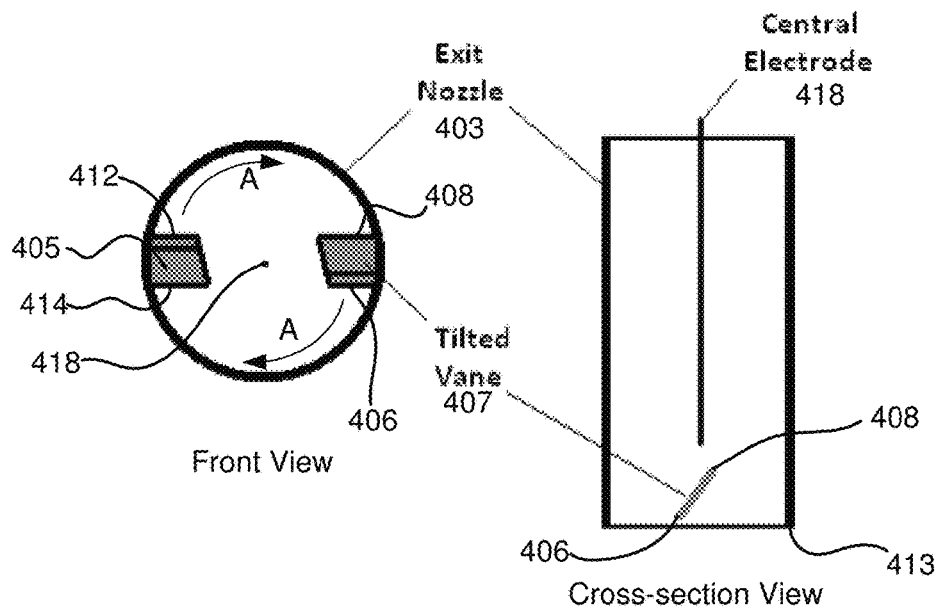
FIG. 8 illustrates tilted vanes within an exit nozzle of the cold plasma beam applicator for improved mixing of ambient air and a carrier gas in accordance with an embodiment of the present disclosure.

The tilted vanes 405, 407 are configured to impart a tangential velocity component onto an inert carrier gas that is exiting nozzle 403 (where the tangential velocity component is denoted by the letter "A") in the front view of FIG. 8. Again, an important consideration is to not induce too much tangential velocity that compromises the plasma beam stability through turbulence. The tangential velocity component imparted onto the inert carrier gas causes the inert carrier gas to mix more effectively with the ambient air outside of distal end 413 of exit nozzle 403 to increase the production of radical species. Although two tilted vanes 405, 407 are shown in FIG. 8, it is to be appreciated that in other embodiments more or less than two tilted vanes may be disposed on an inner surface of exit nozzle 403 to impart a tangential velocity component onto the inert carrier gas exiting nozzle 403.

As stated above, the tilted vanes 403, 407 may be part of an end effector that is included in any of applicators 14, 100, 200 to increase the production of radical species. For example, in one embodiment, vanes 405, 407 may be disposed on an inner surface of the distal end of the fluid flow housing 29 as shown in FIG. 1. In another embodiment, vanes 405, 407 may be disposed on an inner surface of the wall of distal end 206 of tube 204 of applicator 200. In this embodiment, when inert gas is provided through tube 204, as the inert gas exits distal end 206 of tube 204, vanes 405, 407 are configured to impart a tangential velocity component onto the inert gas. The tangential velocity component imparted onto the inert gas causes the inert gas to mix with the ambient air outside of the distal end 206 of tube 204 more effectively, thus increasing the production of radical species.

Figure 9:
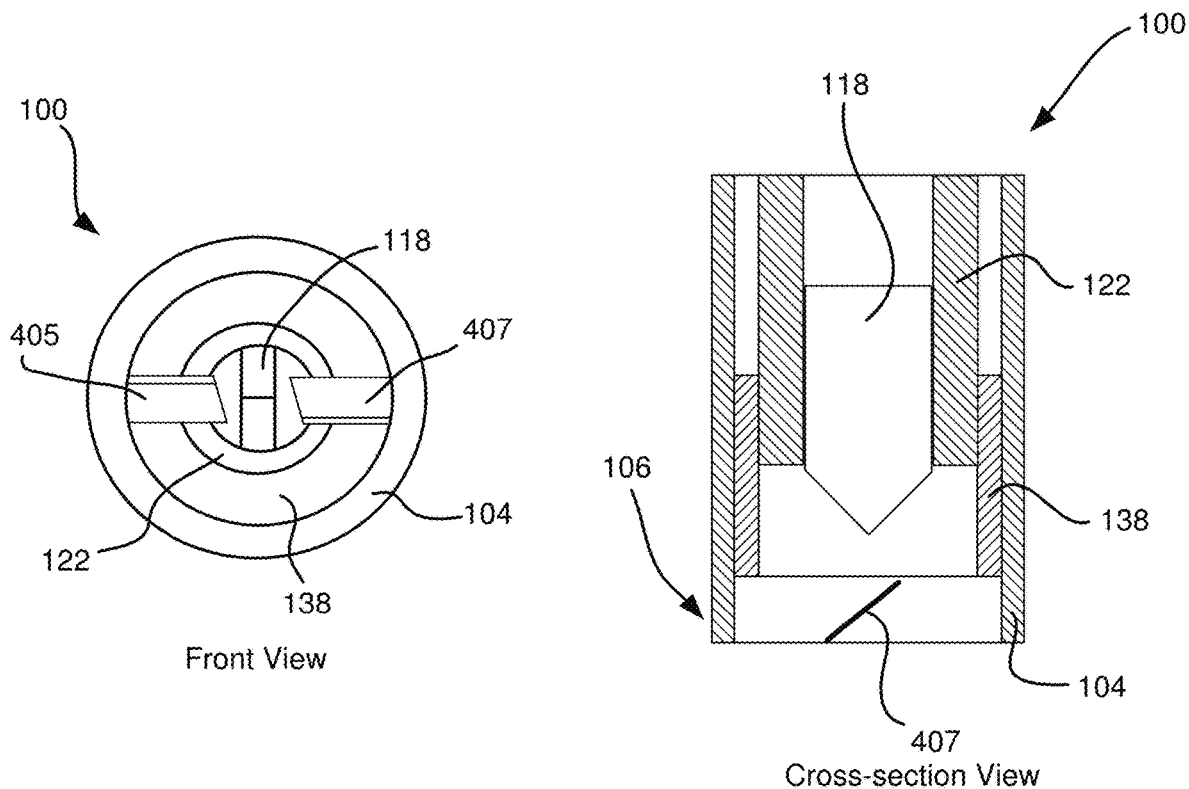
FIG. 9 illustrates the electrosurgical apparatus of FIG. 2A including tilted vanes disposed within an outer tube in accordance with an embodiment of the present disclosure.

In another embodiment, vanes 405, 407 may be disposed on an inner surface of the wall of distal end 106 of tube 104 of applicator 100. Referring to FIG. 9, a front view and a partial cross sectional view of applicator 100 including an end effector with tilted vanes 405, 407 is shown in accordance with the present disclosure. As shown in FIG. 9, in this embodiment, the tilted vanes 405, 407 are each coupled to an inner surface of outer tube 104. The tilted vanes 405, 407 are positioned within the interior of outer tube 104, such that, electrically conducting tube 122 may be advanced until electrically conducting tube 122 meets tilted vanes 405, 407 without vanes 405, 407 interfering or touching blade 118. Furthermore, in this embodiment, the length of blade 118 is configured such that when electrically conducting tube 122 is advanced, blade 118 is able to advance past the distal end 106 of outer tube 104 for use in electrosurgical or mechanical cutting. It is to be appreciated that, although vanes 405, 407 are shown in FIG. 9 as being coupled to an inner surface of outer tube 104, in other embodiments, vanes 405, 407 may be coupled to the inner surface of ceramic insert 138 or the inner surface of electrically conducting tube 122.

In the embodiment shown in FIG. 9, when inert gas is provided through electrically conducting tube 122 to the distal end 106 of outer tube 104, vanes 405, 407 are configured to impart a tangential velocity component onto the inert gas. The tangential velocity component imparted onto the inert gas causes the inert gas to mix for effectively with the ambient air outside of distal end 106 of tube 104 to increase the production of radical species.

Figure 10:
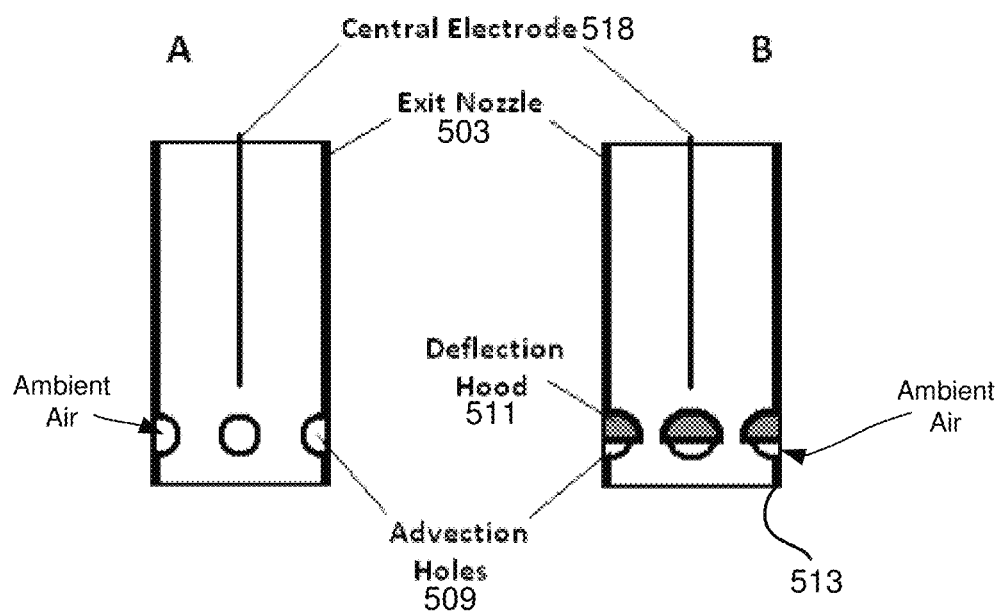
FIG. 10 illustrates an exit nozzle of the cold plasma beam applicator with advection holes for improved mixing of ambient air and a carrier gas in accordance with an embodiment of the present disclosure.

In another embodiment, the end effector is configured as one or more advection apertures in a wall of an outer tube of an applicator, such as one of applicators 14, 100, 200 to induce air into the periphery of the inert carrier gas column. For example, referring to FIG. 10A, an exit nozzle 503 of an applicator, such as applicators 14, 100, 200, is shown including a series of small advection apertures 509 disposed on the wall of the exit nozzle 503 which houses electrode 518. The advection apertures 509 are configured such that when inert carrier gas is passed through exit nozzle 503 and exits a distal end 513 of exit nozzle 503, the inert carrier gas passes by advection apertures 509 and ambient air from the exterior of exit nozzle 503 is drawn through the advection apertures 509 (via the Venturi effect) and into the interior of the exit nozzle 503. In this way, the ambient air drawn in through the advection apertures 509 into the interior of nozzle 503 is mixed with the inert carrier gas in the interior of nozzle 503 to increase the production of radical species.

It is to be appreciated that the design of the diameter and the placement of each aperture 509 is sensitive to a specific carrier gas flow rate, i.e., a diameter of each of the apertures 509 can be tailored or configured to a selected carrier gas flow rate. Too large a hole diameter, or too many holes, may cause the carrier gas to spill out of the apertures 509 rather than provide air advection.

A more robust design is illustrated in FIG. 10B, which relies on the Venturi process to provide air advection over a wider range of carrier gas flows. In the embodiment shown in FIG. 10B, each of the advection holes 509 is partially covered by a deflection hood 511 disposed on an inner surface of the nozzle 503. In this embodiment, a wider range of carrier gas flow rates may be employed since the area of aperture 509 that is covered by deflection hoods 511 may be chosen and configured as desired based on the carrier gas flow rate.

The advection apertures 509 and/or deflection hoods 511 may be part of an end effector that is included in any of applicators 14, 100, 200 to increase the production of radical species. For example, in one embodiment, the advection holes 509 and/or deflection hoods 511 may be positioned at the distal end of the fluid flow housing 29 as shown in FIG. 1. In another embodiment, the advection holes 509 and/or deflection hoods 511 may be positioned in the wall of tube 104 of applicator 100 at the distal end 106. In another embodiment of applicator 100, the apertures 509 may extend through outer wall 104 and the wall of ceramic insert 138. In yet another embodiment, the advection holes 509 and/or deflection hoods 511 may be positioned in the wall of tube 204 of applicator 200. Other configurations and placements of the advection holes and/or deflection hoods are contemplated to be within the scope of the present disclosure.

As an example, when an end effector including apertures 509 and/or deflection hoods 511 is used with applicator 100 (i.e., apertures 509 and deflection hoods 511 are disposed in a wall of the distal end 106 of tube 104), inert gas is provided through electrically conducting tube 122 (while in a retracted position relative to tube 104) and out through the opening of distal end 106 of tube 104. When the inert gas passes the advection apertures 509 and/or deflection hoods 511 in tube 104, the advection apertures 509 and/or deflection hoods 511 are configured to use the Venturi effect to draw ambient air from the exterior of tube 104 to the interior of tube 104. In this way, the ambient air that is drawn in by the advection apertures 509 is more effectively mixed with the inert gas at the distal end 106 of tube 104 to increase the production of radical species.

In another example, when the end effector including apertures 509 and/or deflection hoods 511 is used with applicator 200 (i.e., apertures 509 and deflection hoods are disposed in a wall of the distal end 206 of tube 204), inert gas is provided through tube 206 and out through the opening of distal end 206 of tube 204. When the inert gas passes the advection apertures 509 and/or deflection hoods 511 in tube 204, the advection apertures 509 and/or deflection hoods 511 are configured to use the Venturi effect to draw ambient air from the exterior of tube 204 to the interior of tube 204. In this way, the ambient air drawn in by the advection apertures 509 is more effectively mixed with the inert gas at the distal end 206 of tube 204 to increase the production of radical species.

It is to be appreciated that in some embodiments the mixing strategies of the various end effectors described above in reference to FIGS. 7-10 may be combined to enhance the production of radical species. For example, in one embodiment, an end effector may include advection holes 509 (and/or deflection hoods 511) with vanes 405, 407. In this embodiment, the advection holes 509 (and/or deflection hoods 511) are disposed in the wall of tubes 104, 204 at distal ends 106, 206 and vanes 405, 407 are disposed on an inner surface of the wall of tubes 104, 204 at distal ends 106, 206. In another embodiment, an end effector may include cylindrical augmenter 301 with vanes 305, 307 and vanes 405, 407. In this embodiment, the cylindrical augmenter 301 is disposed over the distal ends 106, 206 of tubes 104, 204 with vanes 305, 307 disposed between cylindrical augmenter 301 and tubes 104, 204 and vanes 405, 407 are disposed on an inner surface of the wall of tubes 104, 204 at distal end 106, 206. It is to be appreciated that, in this embodiment, vanes 305, 307 and vanes 405, 407 may be tilted in the same direction. Alternatively, in this embodiment, vanes 305, 307 may be tilted in an opposite direction to vanes 405, 407.

It is to be appreciated that the various features shown and described are interchangeable, that is a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. An electrosurgical apparatus comprising:
   a housing having a passage extending therethrough;
   a gas flow tube having a proximal end and a distal end, the proximal end of the gas flow tube being at least partially disposed in the passage of the housing;
   an electrode disposed within the gas flow tube and configured to be energized to form plasma at the distal end of the gas flow tube when an inert gas flows through the gas flow tube; and
   a cylindrical augmenter including a distal end and proximal end, the cylindrical augmenter concentrically disposed around the distal end of the gas flow tube, wherein when the inert gas flows through the gas flow tube, the cylindrical augmenter is configured to create a Venturi effect to draw ambient air into an annular space between the proximal end of the cylindrical augmenter and the gas flow tube to mix the ambient air with the insert gas to increase radical species production in the plasma.

2. The electrosurgical apparatus of claim 1, wherein the cylindrical augmenter includes at least one first tilted vane coupled to an inner surface of the cylindrical augmenter and to an exterior surface of the gas flow tube, the at least one first tilted vane configured to impart a tangential velocity component to the ambient air drawn into the annular space between the proximal end of the cylindrical augmenter and the gas flow tube.

3. The electrosurgical apparatus of claim 2, wherein the gas flow tube includes at least one second tilted vane disposed on an inner surface of the gas flow tube.

4. The electrosurgical apparatus of claim 3, wherein the at least one first tilted vane is tilted in a different direction than the at least one second tilted vane.

5. The electrosurgical apparatus of claim 1, further comprising at least one tilted vane disposed on an inner surface of the gas flow tube, the at least one tilted vane configured to impart a tangential velocity component to the inert gas.

6. The electrosurgical apparatus of claim 1, further comprising at least one advection aperture in a distal portion of a wall of the gas flow tube.

7. The electrosurgical apparatus of claim 6, further comprising at least one deflection hood coupled to the gas flow tube, the at least one deflection hood configured to at least partially cover the at least one advection aperture.

8. The electrosurgical apparatus of claim 7, further comprising at least one tilted vane disposed on an inner surface of the gas flow tube.

9. The electrosurgical apparatus of claim 1, wherein the cylindrical augmenter includes at least two tilted vanes diametrically opposed on an inner surface of the cylindrical augmenter to impart a tangential velocity component to the ambient air drawn into the annular space between the proximal end of the cylindrical augmenter and the gas flow tube.

10. An electrosurgical apparatus comprising:
    a housing having a passage extending therethrough, the housing having a proximal end and a distal end;
    an electrically conducting tube having a proximal end and a distal end, the electrically conducting tube at least partially disposed in the passage of the housing;
    an insulating outer tube having a proximal end and a distal end, the insulating outer tube disposed around the electrically conducting tube with the proximal end of the insulating outer tube coupled to the distal end of the housing, the electrically conducting tube being movable along a longitudinal axis of the housing and insulating outer tube;
    an electrode coupled to the distal end of the electrically conducting tube, wherein, in a first position of the electrically conducting tube, the electrode extends beyond the distal end of the insulating outer tube and, in a second position of the electrically conducting tube, the electrode is retracted within the insulating outer tube and is energized via the electrically conducting tube to form plasma when an inert gas flows through the electrically conducting tube; and
    a cylindrical augmenter including a distal end and proximal end, the cylindrical augmenter concentrically disposed around the distal end of the insulating outer tube, wherein when the inert gas flows through the electrically conducting tube, the cylindrical augmenter is configured to create a Venturi effect to draw ambient air into the annular space between the proximal end of the cylindrical augmenter and the insulating outer tube to mix the ambient air with the inert gas to increase radical species production in the plasma.

11. The electrosurgical apparatus of claim 10, wherein the cylindrical augmenter includes at least one first tilted vane coupled to an inner surface of the cylindrical augmenter and to an exterior surface of the insulating outer tube, the at least one first tilted vane configured to impart a tangential velocity component to the ambient air drawn into the annular space between the proximal end of the cylindrical augmenter and the insulating outer tube.

12. The electrosurgical apparatus of claim 11, wherein the insulating outer tube includes at least one second tilted vane disposed on an inner surface of the insulating outer tube.

13. The electrosurgical apparatus of claim 12, wherein the at least one first tilted vane is tilted in a different direction than the at least one second tilted vane.

14. The electrosurgical apparatus of claim 10, further comprising at least one tilted vane disposed on an inner surface of the insulating outer tube, the at least one tilted vane configured to impart a tangential velocity component to the inert gas.

15. The electrosurgical apparatus of claim 10, further comprising at least one advection aperture in a distal portion of a wall of the insulating outer tube.

16. The electrosurgical apparatus of claim 15, further comprising at least one deflection hood coupled to the insulating outer tube, the at least one deflection hood configured to at least partially cover the at least one advection aperture.

17. The electrosurgical apparatus of claim 16, further comprising at least one tilted vane disposed on an inner surface of the insulating outer tube.

18. The electrosurgical apparatus of claim 10, wherein the cylindrical augmenter includes at least two tilted vanes diametrically opposed on an inner surface of the cylindrical augmenter to impart a tangential velocity component to the ambient air drawn into the annular space between the proximal end of the cylindrical augmenter and insulating outer tube.

\* \* \* \* \*